(12) United States Patent
Albadawi et al.

(10) Patent No.: US 9,949,694 B2
(45) Date of Patent: *Apr. 24, 2018

(54) HEART RATE CORRECTION

(71) Applicant: Microsoft Technology Licensing, LLC, Redmond, WA (US)

(72) Inventors: Haithem Albadawi, Redmond, WA (US); Han Yee Mimi Fung, Bellevue, WA (US); Zongyi Liu, Issaquah, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/013,886

(22) Filed: Feb. 2, 2016

(65) Prior Publication Data

US 2017/0095212 A1    Apr. 6, 2017

Related U.S. Application Data

(60) Provisional application No. 62/237,404, filed on Oct. 5, 2015.

(51) Int. Cl.
*A61B 5/00* (2006.01)
*A61B 5/024* (2006.01)
*A61B 5/11* (2006.01)

(52) U.S. Cl.
CPC .......... *A61B 5/721* (2013.01); *A61B 5/02416* (2013.01); *A61B 5/02438* (2013.01);
(Continued)

(58) Field of Classification Search
CPC ... A61B 5/721; A61B 5/6801; A61B 5/02438; A61B 5/1118; A61B 5/112; A61B 5/02416; A61B 5/1123
See application file for complete search history.

(56) References Cited

U.S. PATENT DOCUMENTS 5,243,993 A * 9/1993 Alexander ........... A61B 5/0245
600/517
6,135,951 A 10/2000 Richardson et al.
(Continued)

FOREIGN PATENT DOCUMENTS

KR    20050017254    2/2005
KR    20110088644 A  8/2011
(Continued)

OTHER PUBLICATIONS

ISA European Patent Office, International Search Report and Written Opinion Issued in PCT Application No. PCT/US2016/054031, dated Dec. 21, 2016, WIPO, 11 pages.
(Continued)

*Primary Examiner* — Catherine Voorhees
(74) *Attorney, Agent, or Firm* — Alleman Hall Creasman & Tuttle LLP

(57) ABSTRACT

A wearable heart rate monitoring device includes an optical sensor configured to translate test light reflected from a wearer of the wearable heart rate monitoring device into a machine-readable heart rate signal. The wearable heart rate monitoring device also includes a motion sensor configured to translate motion of the wearable heart rate monitoring device into a machine-readable motion signal. The wearable heart rate monitoring device also includes a heart rate reporting machine, configured to determine a type of activity currently being performed by the wearer of the wearable heart rate monitoring device based at least in part on the machine-readable motion signal, and output an estimated heart rate based on at least the machine-readable heart rate signal and the type of activity.

20 Claims, 8 Drawing Sheets

(52) U.S. Cl.
CPC ............ *A61B 5/112* (2013.01); *A61B 5/1118* (2013.01); *A61B 5/1123* (2013.01); *A61B 5/6801* (2013.01); *A61B 5/7221* (2013.01)

(56) References Cited

U.S. PATENT DOCUMENTS

| | | | |
|---|---|---|---|
| 6,334,065 | B1 | 12/2001 | Al-Ali et al. |
| 6,905,470 | B2 | 6/2005 | Lee et al. |
| 8,475,370 | B2 | 7/2013 | McCombie et al. |
| 8,583,402 | B2 | 11/2013 | Yuen et al. |
| 8,827,906 | B2 | 9/2014 | Yuen et al. |
| 8,961,415 | B2 | 2/2015 | LeBoeuf et al. |
| 2006/0111623 | A1 | 5/2006 | Stetson |
| 2008/0255436 | A1 | 10/2008 | Baker |
| 2009/0112111 | A1 | 4/2009 | Shimizu et al. |
| 2010/0113948 | A1 | 5/2010 | Yang et al. |
| 2012/0083705 | A1 | 4/2012 | Yuen et al. |
| 2012/0190948 | A1 | 7/2012 | Vetter et al. |
| 2014/0058217 | A1 | 2/2014 | Giovangrandi |
| 2014/0058272 | A1 | 2/2014 | Naing et al. |
| 2014/0121540 | A1 | 5/2014 | Raskin |
| 2014/0213858 | A1 | 7/2014 | Presura et al. |
| 2014/0213863 | A1 | 7/2014 | Loseu et al. |
| 2014/0275854 | A1* | 9/2014 | Venkatraman ......... A61B 5/721 600/301 |
| 2014/0316305 | A1 | 10/2014 | Venkatraman et al. |
| 2015/0080746 | A1* | 3/2015 | Bleich ................ A63B 69/0028 600/479 |
| 2015/0196256 | A1* | 7/2015 | Venkatraman ......... A61B 5/721 600/301 |
| 2017/0095169 | A1* | 4/2017 | Liu .................... A61B 5/02416 |

FOREIGN PATENT DOCUMENTS

| | | |
|---|---|---|
| KR | 20030081903 A | 10/2013 |
| WO | 2015069124 A1 | 5/2015 |
| WO | 2015087164 A1 | 6/2015 |
| WO | 2015102589 A1 | 7/2015 |
| WO | 2015139930 A1 | 9/2015 |

OTHER PUBLICATIONS

Peng, et al., "A Comb Filter Based Signal Processing Method to Effectively Reduce Motion Artifacts From Photoplethysmographic Signals", In Physiological Measurement, vol. 36, No. 10, Sep. 3, 2015, 3 pages.

Yan, et al., "An Efficient Motion-Resistant Method for Wearable Pulse Oximeter", In Proceedings of IEEE Transactions on Information Technology in Biomedicine, vol. 12, Issue 3, May 2008, pp. 399-405.

Couceiro, R. et al., "Detection of motion artifacts in photoplethysmographic signals based on time and period domain analysis," Proceedings of the 34th Annual International Conference of the IEEE EMBS, Aug. 28, 2012, San Diego, California, 4 pages.

Yousefi, R. et al., "Adaptive Cancellation of Motion Artifact in Wearable Biosensors," Proceedings of the 34th Annual International Conference of the IEEE EMBS, Aug. 28, 2012, San Diego, California, 5 pages.

Zhang, Z., "Heart Rate Monitoring from Wrist-Type Photoplethysmographic (PPG) Signals During Intensive Physical Exercise," Proceedings of the 2014 IEEE Global Conference on Signal and Information Processing (GlobalSIP 2014), Dec. 3, 2014, Atlanta, Georgia, 5 pages.

Zhang, Z. et al., "TROIKA: A General Framework for Heart Rate Monitoring Using Wrist-Type Photoplethysmographic Signals During Intensive Physical Exercise," IEEE Transactions on Biomedical Engineering, vol. 62, No. 2, Feb. 2015, Published Online Sep. 19, 2014, 10 pages.

Peng, F. et al., "A comb filter based signal processing method to effectively reduce motion artifacts from photoplethysmographic signals," Physiological Measurement, vol. 36, No. 10, Oct. 2015, Published Online Sep. 3, 2015, 12 pages.

"Second Written Opinion Issued in PCT Application No. PCT/US2016/054031", dated Aug. 18, 2017, 6 Pages.

* cited by examiner

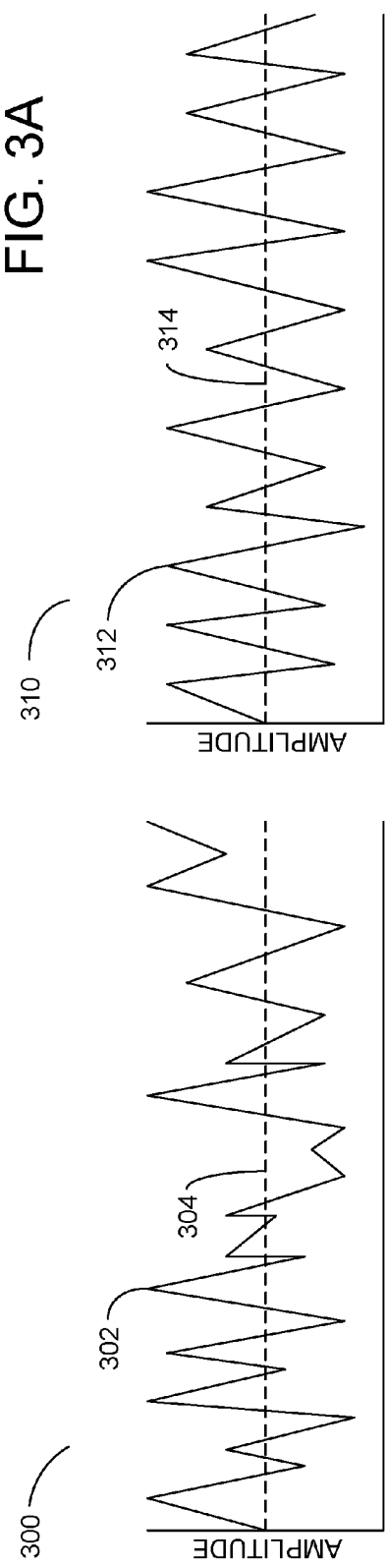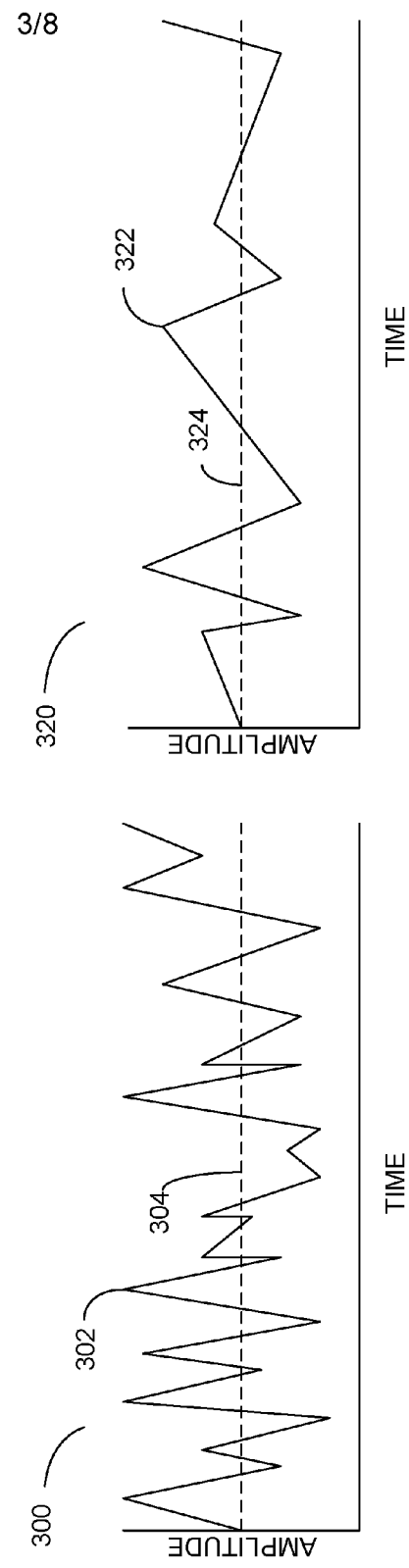

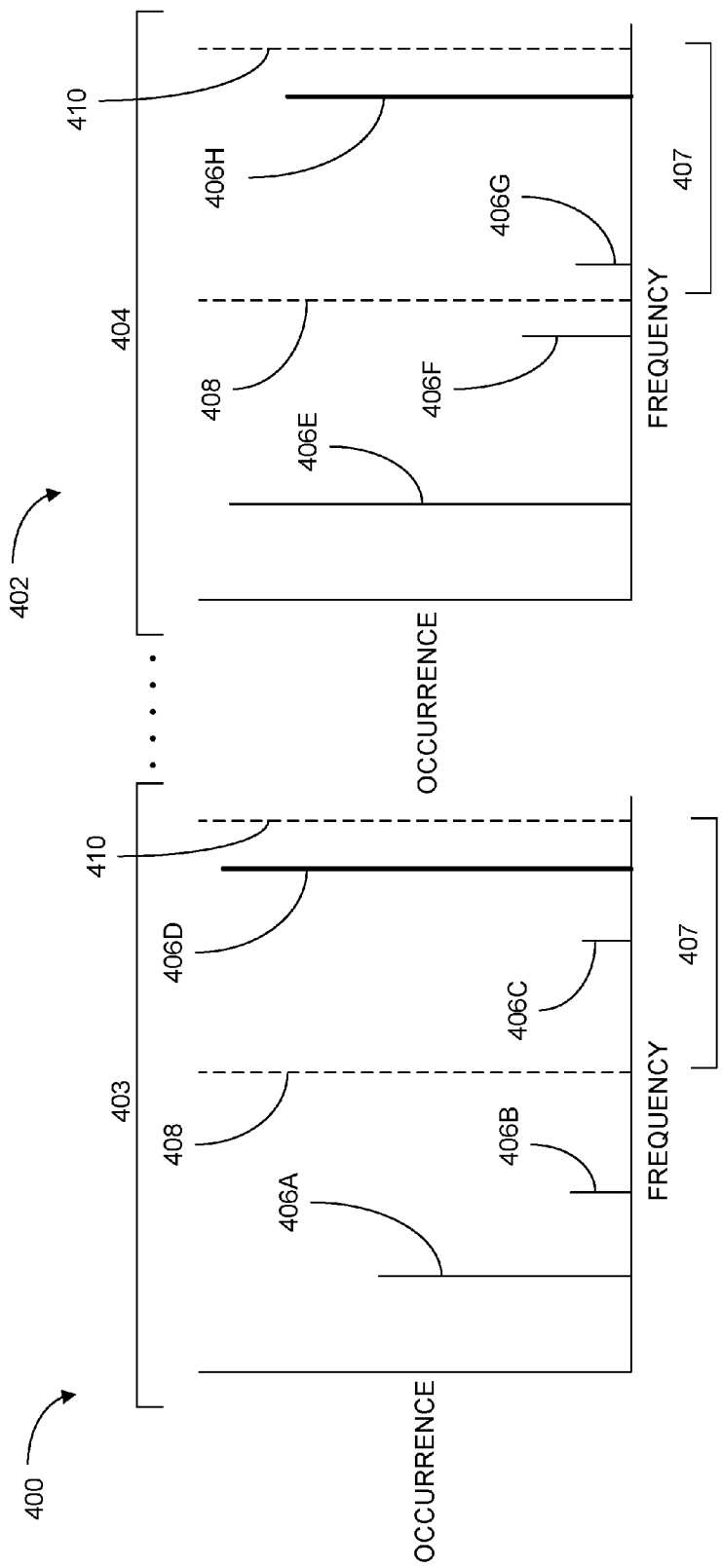

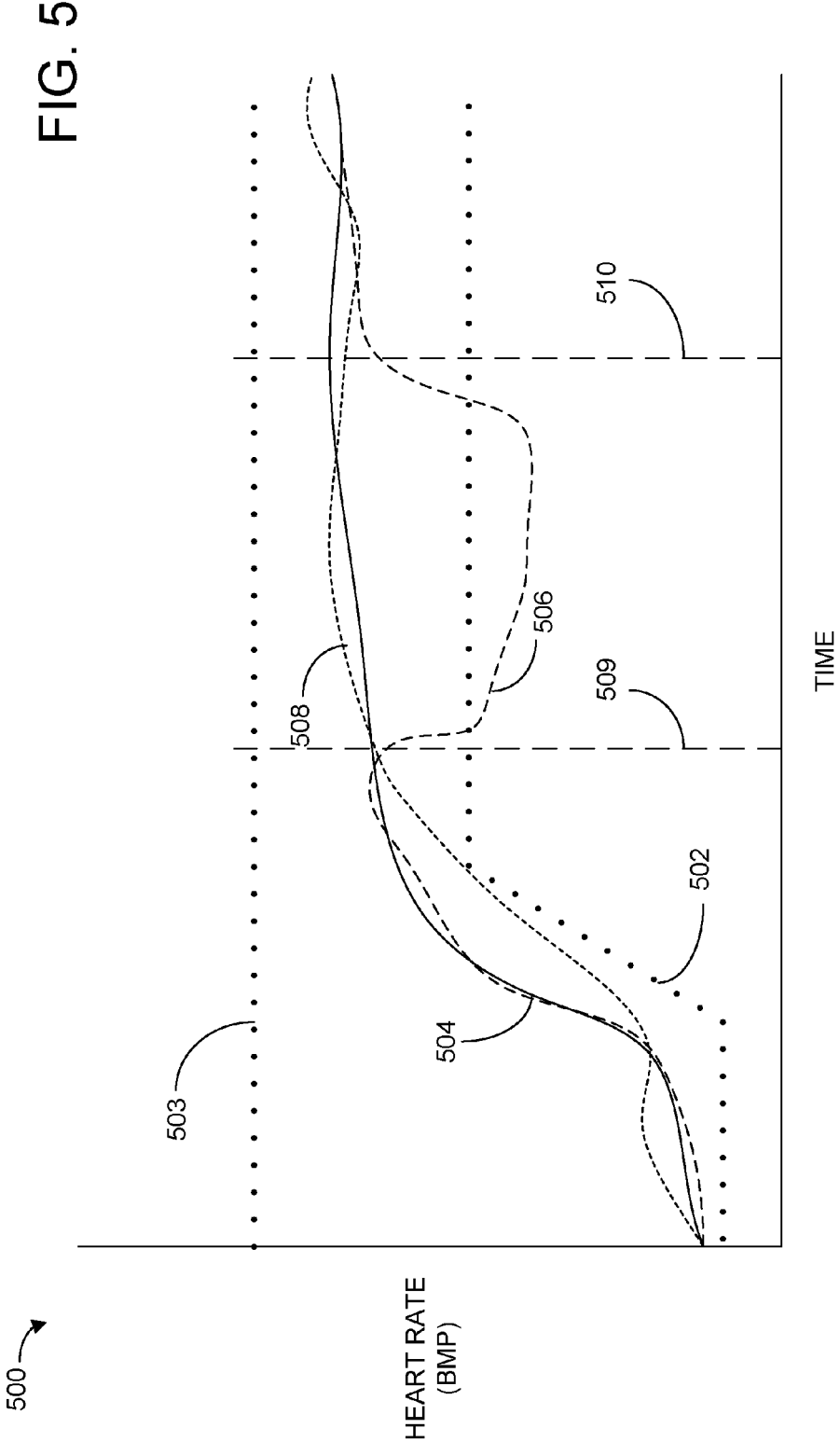

HEART RATE CORRECTION

CROSS REFERENCE TO RELATED APPLICATIONS

This application claims priority to U.S. Provisional Patent Application No. 62/237,404, filed Oct. 5, 2015, the entirety of which is hereby incorporated herein by reference.

BACKGROUND

Many people find it helpful and informative to track their own heart rate, in particular during periods of exercise. A variety of wearable devices exist which are usable for tracking heart rate.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

A wearable heart rate monitoring device includes an optical sensor configured to translate test light reflected from a wearer of the wearable heart rate monitoring device into a machine-readable heart rate signal. The wearable heart rate monitoring device also includes a motion sensor configured to translate motion of the wearable heart rate monitoring device into a machine-readable motion signal. The wearable heart rate monitoring device also includes a heart rate reporting machine, configured to determine a type of activity currently being performed by the wearer of the wearable heart rate monitoring device based at least in part on the machine-readable motion signal, and output an estimated heart rate based on at least the machine-readable heart rate signal and the type of activity.

BRIEF DESCRIPTION OF THE DRAWINGS

FIGS. 3A and 3B show example motion-corrected heart rate signals.

FIG. 4 shows example frequency domain representations of a machine-readable heart rate signal.

FIG. 5 shows a graph of a wearer's measured running heart rate before and after correction.

DETAILED DESCRIPTION

A common function of wearable electronic devices is the measurement of wearer heart rate. However, many techniques for heart rate measurement are susceptible to signal contamination, compromising the accuracy of the measured heart rate. For example, during exercise, a measured heart rate signal may be contaminated by a motion (e.g., footfalls) of the wearer of the heart rate monitoring device.

Techniques exist which are usable to mitigate motion contamination in a heart rate signal, potentially returning a more accurate heart rate measurement. However, these techniques are not effective at removing signal contamination in all circumstances. For example, when a frequency of a wearer's motion or its harmonics is similar to the wearer's heart rate, motion correction may also remove the heart rate signal, making the wearer's heart rate difficult to determine. In some cases, even after motion correction, a wearable heart rate monitoring device may still track harmonics of a wearer's motion, resulting in an inaccurate heart rate measurement. Further, in situations where a signal-to-noise ratio (SNR) of a heart rate signal is relatively low, a wearable heart rate monitoring device may have difficulty accurately distinguishing a wearer's heart rate from background contamination.

Accordingly, the present disclosure is directed to a technique for correcting a heart rate measured by a wearable heart rate monitoring device. The technique includes estimating a wearer's current heart rate using a first estimation approach. The first estimation approach may include motion-correcting a machine-readable heart rate signal, then performing z-crossing in order to determine a first candidate heart rate, as will be describe below. The technique also includes estimating the wearer's heart rate using a second, different estimation approach. The second estimation approach may include identifying highest occurrence frequencies in a frequency search window of a frequency domain representation of the machine-readable heart rate signal, where the range of the search window varies according to the type of activity the wearer of the wearable heart rate monitoring device is currently performing. If a majority of the highest occurrence frequencies identified in the search window over a plurality of time intervals fall within a similarity threshold, an average highest occurrence frequency (e.g., in beats per minute) may be identified as a second candidate heart rate. The candidate heart rate which is determined to be more consistent with the type of activity being performed by the user may be output for further processing, and/or displayed to the wearer.

Figure 1A:
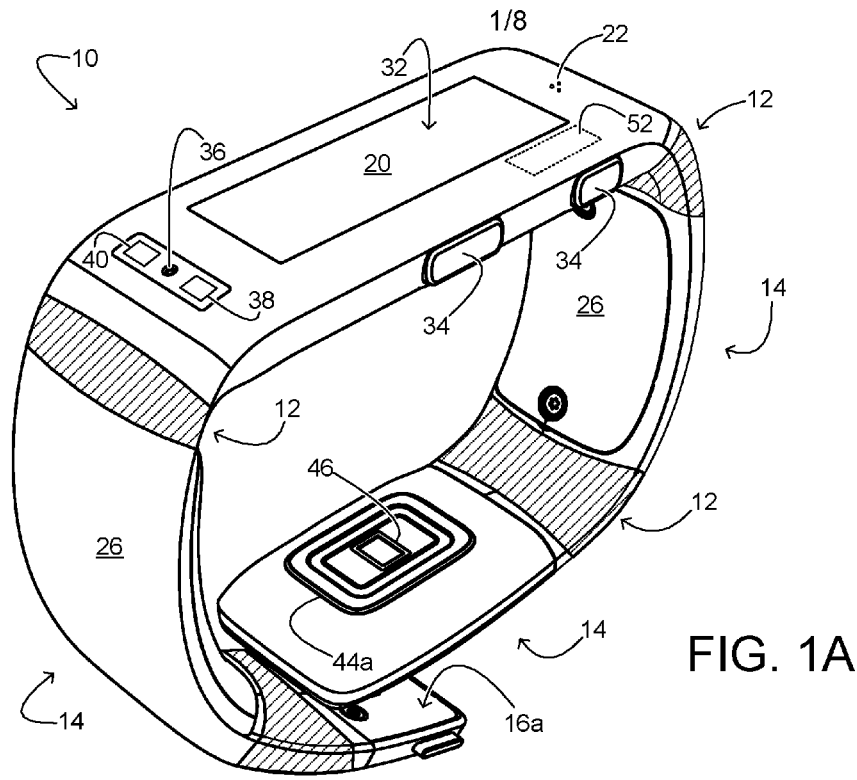
FIGS. 1A and 1B show an example wearable heart rate monitoring device.
Figure 1B:
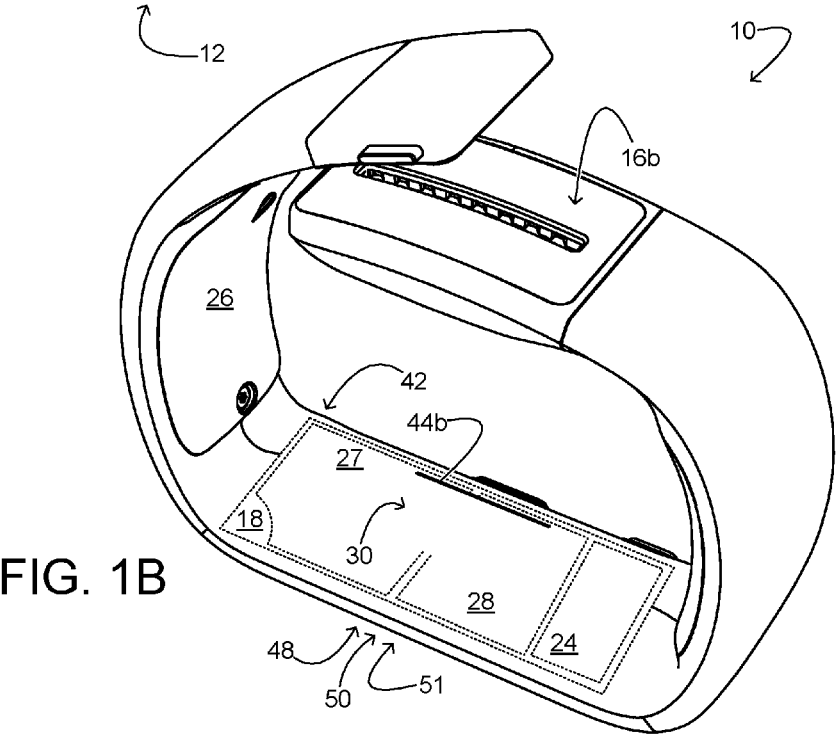

FIGS. 1A and 1B show aspects of an example sensory-and-logic system in the form of a wearable heart rate monitoring device 10, which may be usable to estimate a wearer's heart rate. The illustrated device is band-shaped and may be worn around a wrist. Device 10 includes at least four flexion regions 12 linking less flexible regions 14. The flexion regions of device 10 may be elastomeric in some examples. Fastening componentry 16A and 16B is arranged at both ends of the device. The flexion regions and fastening componentry enable the device to be closed into a loop and to be worn on a user's wrist. In other implementations, wearable heart rate monitoring devices of a more elongate band shape may be worn around the user's bicep, waist, chest, ankle, leg, head, or other body part. The device, for example, may take the form of eye glasses, a headband, an arm-band, an ankle band, a chest strap, or an implantable device to be implanted in tissue.

Wearable heart rate monitoring device 10 includes various functional components integrated into regions 14. In particular, the heart rate monitoring device includes a compute system 18, display 20, loudspeaker 22, communication suite 24, and various sensors. These components draw power from one or more energy-storage cells 26. A battery--e.g., a lithium ion battery-is one type of energy-storage cell suitable for this purpose. Examples of alternative energy-storage cells include super- and ultra-capacitors. In devices worn on the user's wrist, the energy-storage cells may be curved to fit the wrist, as shown in the drawings.

In general, energy-storage cells 26 may be replaceable and/or rechargeable. In some examples, recharge power may be provided through a universal serial bus (USB) port 30, which includes a magnetic latch to releasably secure a complementary USB connector. In other examples, the energy storage cells may be recharged by wireless inductive or ambient-light charging. In still other examples, the wearable heart rate monitoring device may include electromechanical componentry to recharge the energy storage cells from the user's adventitious or purposeful body motion. For example, batteries or capacitors may be charged via an electromechanical generator integrated into device 10. The generator may be turned by a mechanical armature that turns while the user is moving and wearing device 10.

In wearable heart rate monitoring device 10, compute system 18 is situated below display 20 and operatively coupled to the display, along with loudspeaker 22, communication suite 24, and the various sensors. The compute system includes a data-storage machine 27 to hold data and instructions, and a logic machine 28 to execute the instructions. The compute system may include one or more hardware sensor interfaces configured to receive and interpret inputs from the various sensors. Such hardware sensor interfaces may receive inputs via electrical transmission over physical conductors (e.g., an electronic bus), light transmission over optical conveyances (e.g., fiber optics), electromagnetic signals conveyed over the air (e.g., radio frequency transmission), etc. Aspects of the compute system are described in further detail with reference to FIG. 8.

Display 20 may be any suitable type of display. In some configurations, a thin, low-power light emitting diode (LED) array or a liquid-crystal display (LCD) array may be used. An LCD array may be backlit in some implementations. In other implementations, a reflective LCD array (e.g., a liquid crystal on silicon, LCOS array) may be frontlit via ambient light. A curved display may also be used. Further, AMOLED displays or quantum dot displays may be used.

Communication suite 24 may include any appropriate wired or wireless communications componentry. In FIGS. 1A and 1B, the communications suite includes USB port 30, which may be used for exchanging data between wearable heart rate monitoring device 10 and other computer systems, as well as providing recharge power. The communication suite may further include two-way Bluetooth, Wi-Fi, cellular, near-field communication and/or other radios. In some implementations, the communication suite may include an additional transceiver for optical, line-of-sight (e.g., infrared) communication.

In wearable heart rate monitoring device 10, touch-screen sensor 32 is coupled to display 20 and configured to receive touch input from the user. The touch sensor may be resistive, capacitive, or optically based. Pushbutton sensors may be used to detect the state of push buttons 34, which may include rockers. Input from the pushbutton sensors may be used to enact a home-key or on-off feature, control audio volume, turn the microphone on or off, etc.

FIGS. 1A and 1B show various other sensors of wearable heart rate monitoring device 10. Such sensors include microphone 36, visible-light sensor 38, ultraviolet sensor 40, and ambient temperature sensor 42. The microphone provides input to compute system 18 that may be used to measure the ambient sound level or receive voice commands from the wearer. Input from the visible-light sensor, ultraviolet sensor, and ambient temperature sensor may be used to assess aspects of the wearer's environment--i.e., the temperature, overall lighting level, and whether the wearer is indoors or outdoors.

FIGS. 1A and 1B show a pair of contact sensor modules 44A and 44B, which contact the wearer's skin when wearable heart rate monitoring device 10 is worn. The contact sensor modules may include independent or cooperating sensor elements, to provide a plurality of sensory functions. For example, the contact sensor modules may provide an electrical resistance and/or capacitance sensory function, which measures the electrical resistance and/or capacitance of the wearer's skin Compute system 18 may use such input to assess whether or not the device is being worn, for instance. In some implementations, the sensory function may be used to determine how tightly the wearable heart rate monitoring device is being worn. In the illustrated configuration, the separation between the two contact-sensor modules provides a relatively long electrical path length, for more accurate measurement of skin resistance. In some examples, a contact sensor module may also provide measurement of the wearer's skin temperature. Arranged inside contact sensor module 44B in the illustrated configuration is the optical heart rate sensor 46. The optical heart rate sensor may include an optical source and matched optical sensor to detect blood flow through the capillaries in the skin and thereby provide a measurement of the wearer's heart rate, blood oxygen level, blood glucose level, or other biomarkers with optical properties. Further details regarding the optical heart rate sensor, optical source, and optical sensor are provided with reference to FIG. 2.

Wearable heart rate monitoring device 10 may also include motion sensing componentry, such as an accelerometer 48, gyroscope 50, and magnetometer 51. The accelerometer and gyroscope may furnish inertial and/or rotation rate data along three orthogonal axes as well as rotational data about the three axes, for a combined six degrees of freedom. This sensory data can be used to provide a pedometer/calorie-counting function, for example. Data from the accelerometer and gyroscope may be combined with geomagnetic data from the magnetometer to further define the inertial and rotational data in terms of geographic orientation. The wearable heart rate monitoring device may also include a global positioning system (GPS) receiver 52 for determining the wearer's geographic location and/or velocity. In some configurations, the antenna of the GPS receiver may be relatively flexible and extend into flexion regions 12.

Compute system 18, via the sensory functions described herein, is configured to acquire various forms of information about the wearer of wearable heart rate monitoring device 10. Such information must be acquired and used with utmost respect for the wearer's privacy. Accordingly, the sensory functions may be enacted subject to opt-in participation of the wearer. In implementations where personal data is collected on the device and transmitted to a remote system for processing, that data may be anonymized. In other examples, personal data may be confined to the wearable heart rate monitoring device, and only non-personal, summary data transmitted to the remote system.

Figure 2:
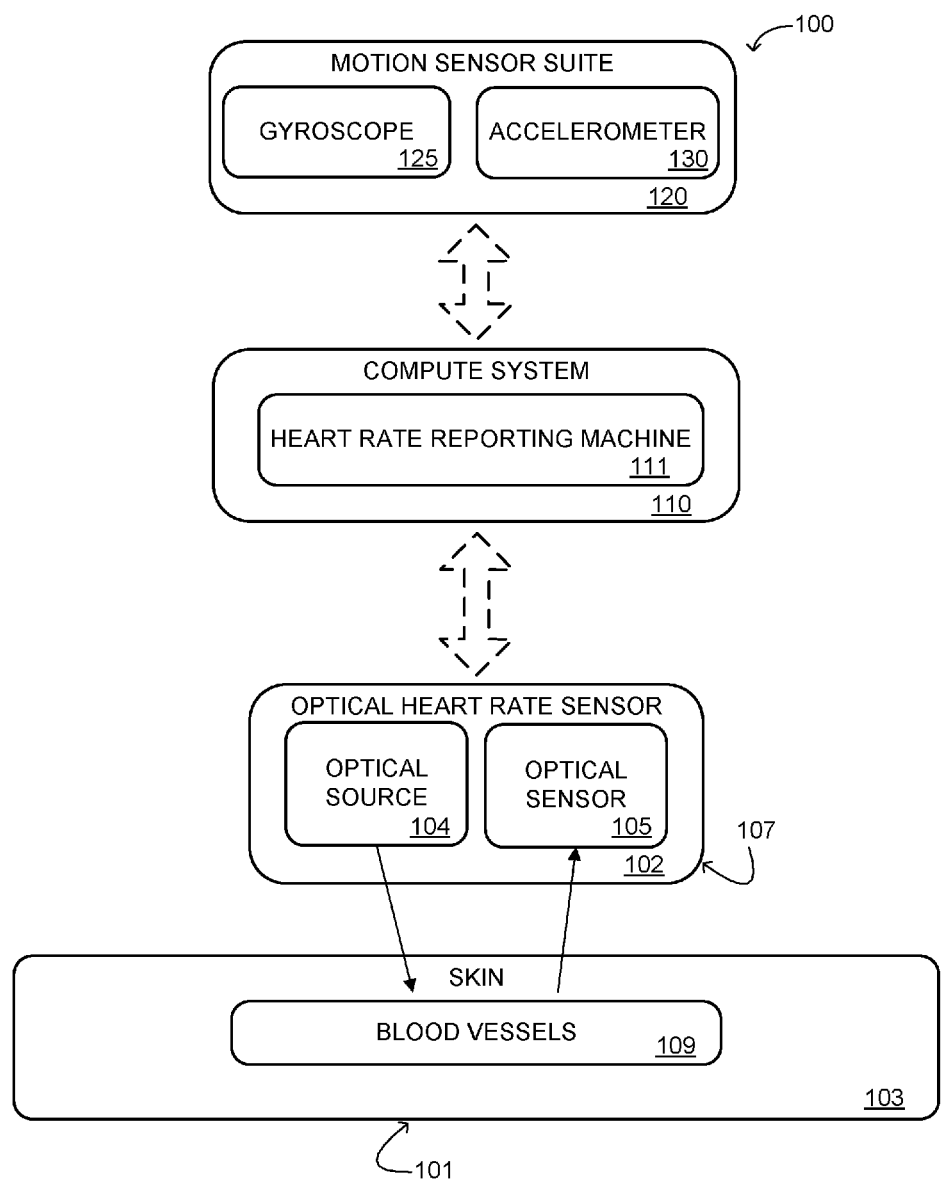
FIG. 2 schematically shows an example optical sensor, motion sensor suite, and compute system that may be included in the wearable heart rate monitoring device of FIGS. 1A-1B.

FIG. 2 shows a schematic depiction of a sensory-and-logic system 100 coupled to the wrist of a wearer 101 so that an optical heart rate sensor 102 is adjacent to the skin 103 of wearer 101. Optical heart rate sensor 102 comprises an optical source 104 configured to illuminate with a test light one or more blood vessels through the skin of the wearer, and an optical sensor 105, configured to measure reflected test light from the blood vessels, thus comprising a photoplethysmogram (PPG) sensor. Optical source 104 may comprise one or more LED emitters, for example, while optical sensor 105 may comprise one or more photodiodes matched to detect light at frequencies that are based on the frequencies of light output by the optical source. Optical heart rate sensor 102 may be coupled within a housing 107 configured to promote contact between sensor 102 and skin 103, and further configured to block, filter, or otherwise limit ambient light from reaching the optical sensor. In this way, the majority of light reaching optical sensor 105 may be light originating from optical source 104 that has reflected off of blood vessels 109 beneath skin 103. As an example, FIG. 1A shows a wearable heart rate monitoring device 10 that is configured to position optical heart rate sensor 46 such that its optical source may illuminate capillaries located beneath the skin of the wearer's forearm while the wearable heart rate monitoring device is worn by the wearer. In other configurations, an optical heart rate sensor may be positioned within a wearable heart rate monitoring device such that an optical source illuminates a radial artery through the skin of the wearer while the wearable heart rate monitoring device is worn by the wearer. Alternatively, an optical heart rate sensor and its associated compute system may be housed separately and configured to communicate via a communication suite. For example, an optical heart rate sensor may be included in a headset and configured to illuminate capillaries located in the wearer's ear lobe while the headset is worn by the wearer, while the compute system resides within a wrist-worn computing device configured to communicate with the headset, via wireless communication, for example. An optical sensor may be configured to sense light reflected off of blood vessels located beneath the skin of the wearer (e.g., wrist worn), or the optical sensor may be configured to sense light transmitted through blood vessels located beneath the skin of the user (e.g., ear worn).

Compute system 110 may comprise heart rate reporting machine 111. Heart rate reporting machine 111 may provide control signals to optical source 104 and optical sensor 105. Heart rate reporting machine 111 may receive raw signals from optical sensor 105, and may further process the raw signals to a machine-readable heart rate signal, usable to determine heart rate, caloric expenditures, etc., as well as perform other operations, such as estimating candidate heart rates, comparing candidate heart rates to a machine-readable wearer activity signal, and outputting candidate heart rates for further processing and/or display to the wearer. Processed signals may be stored and output via compute system 110. Control signals sent to optical source 104 and optical sensor 105 may be based on signals received from optical sensor 105, one or more motion sensors, ambient light sensors, information stored in compute system 110, input signals, etc.

The signal from the optical sensor may degrade in quality with increased motion, as wearer motion may change the optical properties of the skin, tissues, and blood vessels beneath the optical sensor. Further, wearer motion may impact the movement of blood and other fluids through the user's tissue. As such, the signal output by the optical sensor may be filtered or otherwise adjusted based on wearer movement prior to determining a heart rate of the wearer. Sensory-and-logic system 100 may include a motion sensor suite 120 communicatively coupled to compute system 110. Signals from motion sensor suite 120 may be provided to heart rate reporting machine 111. Motion sensor suite 120 may include gyroscope 125 and accelerometer 130. Gyroscope 125 and accelerometer 130 may each be three-axis motion sensors. Accordingly, gyroscope 125 and accelerometer 130 may record and transmit signal channels for each axis.

As described above, a wearer heart rate signal, such as the machine-readable heart rate signal processed by compute system 110, may be contaminated and/or degraded by motion of the wearer of the wearable heart rate monitoring device. Accordingly, it may be desirable to perform one or more motion correction operations on the machine-readable heart rate signal. Motion correction may utilize a machine-readable wearer activity signal, which describes one or more aspects of a current activity of the wearer of the wearable heart rate monitoring device. The machine-readable wearer activity signal may describe a type of activity currently being performed by the user, obtained after the wearable heart rate monitoring device directly prompts the user to identify the type of activity, for example. Additionally or alternatively, the machine-readable heart rate signal may include a machine-readable motion signal S_A, obtained from one or more motion sensors and corresponding to a motion of the wearable heart rate monitoring device. The one or more motion sensors may comprise a gyroscope and/or an accelerometer, as nonlimiting examples. The gyroscope and/or accelerometer may be three-axis motion sensors. In those examples, the machine-readable motion signal S_A output by the motion sensor may comprise a signal channel for each axis. As an example, a machine-readable motion signal S_A may be received from the one or more motion sensors, and a wearer motion frequency MA may be estimated based on the machine-readable motion signal S_A.

The wearer motion frequency MA may correspond to a frequency with which the wearer performs a repetitive physical activity. For example, the motion frequency MA may correspond to a footfall frequency of the wearer, in the event that the wearer is walking, running, hiking, etc. Further, the motion frequency MA may correspond to revolutions per minute achieved by the wearer on an exercise machine, such as a stationary bike, rowing machine, etc. In general, the motion frequency MA may correspond to the frequency at which the wearer performs virtually any physical activity that has one or more repetitive components.

As described above, the machine-readable heart rate signal may arise from a PPG signal, which indicates reflected illumination from one or more blood vessels illuminated by an optical source through a wearer's skin In such an example, performing motion correction on the machine-readable heart rate signal may comprise filtering the motion frequency MA from the PPG heart rate signal S_P, resulting in a motion-corrected heart rate signal S_P'. Filtering the PPG signal S_P based on the motion frequency MA may include applying a comb filter to the PPG signal, although other types of filters or methods of signal processing may be used to remove the motion frequency from the PPG signal in addition to or as an alternative to the comb filter, such as infinite impulse response filters or notch filters.

After motion correction, a time domain representation of the motion-corrected heart rate signal S_P' may be used to estimate a first candidate heart rate of the wearer via a first estimation approach. The motion-corrected heart rate signal S_P' may be analyzed in real time In the first estimation approach, the motion-corrected heart rate signal S_P' may be detrended (i.e., a mean or best fit line subtracted from the motion-corrected heart rate signal). A first candidate heart rate HR may then be estimated based on zero-crossing events of the detrended filtered optical signal. A zero-axis may be determined and applied to the detrended filtered optical signal. Each heart beat comprises two zero-crossing events, a negative-to-positive zero-crossing event, and a positive-to-negative zero-crossing event. As such, the average length of time between alternating zero-crossing events may be used to estimate a first candidate heart rate. In some examples, heart rate may be estimated based on amplitude peaks in addition to or as an alternative to zero crossing events. The length of time between consecutive amplitude peaks may be used to estimate a heart rate of the user. Other approaches of estimating heart rate from a processed optical signal may be used in addition to or as an alternative to the described methods without departing from the scope of this disclosure.

However, the motion compensation and heart rate estimation approach described above may not always provide an accurate measurement of a wearer's heart rate. For example, when a wearer of a wearable heart rate monitoring device begins running at a pace of 150 steps per minute, his heart rate may gradually rise from around 70 beats per minute (bpm) to around 170 bpm. However, the wearable heart rate monitoring device will likely suppress the PPG signal near the 150 bpm frequency for motion correction. Accordingly, the heart rate signal itself may be removed from the machine-readable heart rate signal in addition to the motion-related contamination, compromising the ability of the wearable heart rate monitoring device to provide an accurate measurement of heart rate. Further, it may not be possible to remediate this problem using a signal provided by a motion sensor, given that the wearer's motion frequency may not significantly change throughout durations of the exercise.

Further, in some cases, a wearable heart rate monitoring device may provide an inaccurate measurement of heart rate during situations in which the PPG signal has a relatively low signal-to-noise ratio (SNR). For example, when a wearer of a wearable heart rate monitoring device is walking, his step rate may be approximately 55 steps per minute, and his heart rate may be around 85 bpm. However, even after motion correction, the wearable heart rate monitoring device may detect harmonics from the wearer's footfalls, as well as other sources of signal contamination. As such, the wearable heart rate monitoring device may provide a substantially inaccurate estimation of the wearer's heart rate, even after motion compensation.

FIGS. 3A and 3B show graphs of a time domain representation of a machine-readable heart rate signal amplitude over time, before and after motion correction. Graph 300, shown in both FIGS. 3A and 3B, includes plot 302, indicating the amplitude of a PPG signal over a period of time Graph 300 additionally includes zero-axis 304, which may be determined and applied as described above. Plot 302 crosses zero-axis 304 a number of times. However, not all zero-axis crossing events in graph 300 correspond to wearer heart beats. Rather, at least some zero-axis crossing events in graph 300 are attributable to signal contamination resulting from a motion of the wearer of the wearable heart rate monitoring device.

Accordingly, FIG. 3A also includes graph 310, which has been corrected to compensate for the motion of the wearer. As described above, the wearable heart rate monitoring device may determine a wearer's rate of motion MA, and apply a comb filter to the PPG signal S_P using MA, thus resulting in a corrected PPG signal S_P'. Graph 310 includes plot 312, which indicates the amplitude of the corrected PPG signal over time Further, graph 310 includes a zero-axis 314. In some embodiments, zero-axis 314 may match zero-axis 304. Alternatively, zero-axis 314 may be calculated independently of zero-axis 304, after motion correction has been performed for the signal shown in graph 300. As described above, the wearable heart rate monitoring device may detect zero-axis crossing events in the corrected PPG signal, and use this to estimate a first candidate heart rate of the wearer of the wearable heart rate monitoring device.

However, as described above, applying motion correction to a machine-readable heart rate signal may not always facilitate the accurate estimation of wearer heart rate. This can be seen from graph 320, shown in FIG. 3B. Graph 320 includes plot 322, which shows the motion-corrected PPG signal S_P' over time Additionally, graph 320 includes zero-axis 324. However, in this example, the motion correction applied to graph 300 removed aspects of PPG signal 302 which corresponded to the wearer's heart rate. As a result, little meaningful information can be obtained from graph 320, and the heart rate estimated by the wearable heart rate monitoring device will likely differ significantly from the wearer's actual heart rate.

In order to help alleviate this problem, a wearable heart rate monitoring device may estimate a second candidate heart rate of the wearer based on the machine-readable heart rate signal and using a second estimation approach, which differs from the first estimation approach. In some embodiments, the heart rate signal evaluated may be the motion-corrected heart rate signal S_P', while in other embodiments, the signal evaluated may be the unmodified machine-readable heart rate signal S_P. The second estimation approach may include generating a frequency search window, and applying the frequency search window to a frequency domain representation of the applicable heart rate signal. For each of a plurality of time intervals, the wearable heart rate monitoring device may identify a highest occurrence frequency within the search window. If, for the plurality of time intervals, a majority of the identified highest occurrence frequencies fall within a similarity threshold, an average highest occurrence frequency may be selected as the second candidate heart rate. For example, the similarity threshold may be equal to one standard deviation, a fraction of a standard deviation, a threshold number of beats per minute, etc.

A range of the frequency search window may be based on a number of factors including, for example, the wearer's movement rate MA, as well as the wearer's movement type. In particular, the range may have a different size depending on the frequency of the wearer's motion, as well as the type of activity currently being performed by the wearer (e.g., walking, running, cycling, swimming, etc.). A variety of suitable techniques may be used to identify the type of activity. For example, the machine-readable motion signal S_A, and/or other signals from other hardware sensors, may be compared to a template signal for each type of identifiable activity, and the activity corresponding to the template which most closely matches the sensor signals may be identified as the activity of the wearer. Machine learning may be used to identify the type of activity. Additionally or alternatively, the wearable heart rate monitoring device may prompt the wearer to identify his or her current activity type. Other suitable techniques for identifying the type of activity currently being performed by the wearer may additionally and/or alternatively be utilized.

The upper and lower bounds of the frequency search window may be set in order to capture a range of frequencies including or adjacent to frequencies corresponding to the rate of motion of the wearer, or its harmonics. As nonlimiting examples, when the type of activity is walking, a lower bound of the search window (F_Low) may be equal to the motion rate MA, which may indicate a footfall frequency of the wearer, while the upper bound (F_High) is equal to MA multiplied by two, which may be equal to twice the footfall frequency. Similarly, while the type of activity is running, F_Low may be equal to MA multiplied a constant (e.g., 1, 1.5, 2, etc.), while F_High is equal to 200 bpm. However, in other examples, other search range sizes and/or ranges may be used. In general, the values of F_Low and F_High may be any suitable values, and may differ depending on the type of motion the wearer is performing.

After identifying a highest occurrence frequency within the frequency search window, the identified frequency may be stored in a peak magnitude buffer (PB). Each entry in PB may correspond to a highest occurrence frequency identified during a different interval of time, where an interval of time lasts for any suitable period (e.g., one second, five seconds, ten seconds) and is updated with any suitable frequency (e.g., one second, two seconds). The peak magnitude buffer may have room to store any suitable number of identified frequency values (e.g., a buffer size of 20, 30, etc.). Once PB is full, the wearable heart rate monitoring device compares the frequency values stored in PB to one another. If a threshold (e.g., more than half, more than two thirds, etc.) of the values in PB fall within the similarity threshold, an average of the similar frequency values may be selected as the second candidate heart rate (HR'). Alternatively, a most recently identified highest occurrence frequency, a highest occurrence frequency which is closest to a calculated average, or other frequency value found within the frequency search window for at least one interval of time may be selected as the second candidate heart rate value.

FIG. 4 shows frequency domain representations 400 and 402 of a machine-readable heart rate signal over two intervals of time 403 and 404. Each representation includes a number of frequency peaks 406, where a height of each frequency peak indicates the relative occurrence of each represented frequency in the machine-readable heart rate signal. In representation 400, frequency peak 406D has been identified as representing the highest occurrence frequency in time interval 403. Similarly, frequency peak 406H has been identified as representing the highest occurrence frequency in time interval 404. The frequency values indicated by frequency peaks 406D and 406H may be stored in a buffer PB, as described above, and ultimately compared to other highest occurrence frequencies identified for other time intervals.

Representations 400 and 402 also include frequency search windows 407. Each frequency search window is defined by a lower bound 408 and an upper bound 410. Only frequencies located within the frequency search window may be considered as potential heart rate candidates. For example, in representation 402, frequency peak 406E represents a frequency having a higher occurrence rate within the examined period than the frequency represented by frequency peak 406H. However, the frequency represented by frequency peak 406H is identified as the highest occurrence frequency for time interval 404, as the frequency represented by frequency peak 406E is not found within the frequency search window. As described above, the range of each search window 407, as well as the positions of lower bounds 408 and upper bounds 410, may vary according to a variety of factors, including wearer motion frequency and activity type.

After estimating the first and second candidate heart rates, each candidate heart rate may be evaluated in order to determine whether or not it is more consistent with the machine-readable activity signal than the other candidate heart rate. This evaluation may differ depending on the nature of the wearer's motion, as well as the motion rate MA. For example, when a wearer of the wearable heart rate monitoring device is walking, then the wearable heart rate monitoring device may check whether the second estimated heart rate is lower than the first estimated heart rate. If so, and if the magnitude of the second estimated heart rate is relatively strong in the machine-readable heart rate signal, then the second candidate heart rate is output in lieu of the first candidate heart rate. Otherwise, it is determined that the first candidate heart rate is more consistent with the machine-readable activity signal than the second candidate heart rate, and the first candidate heart rate is output.

Similarly, when a wearer of the wearable heart rate monitoring device is running, then the wearable heart rate monitoring device may compare the second estimated heart rate to the wearer motion frequency. These two values may be compared in any suitable way. For example, the wearable heart rate monitoring device may check to see if the second candidate heart rate is higher than a threshold value. In some embodiments, this threshold value may be equal to 10 bpm more than the motion frequency multiplied by two. If the second candidate heart rate is higher than the threshold, and the magnitude of the second candidate heart rate is relatively strong in the machine-readable heart rate signal, then the second candidate heart rate is determined to be more consistent with the machine-readable activity signal than the first candidate heart rate, and the second candidate heart rate is output. Otherwise, it is determined that the first candidate heart rate is more consistent with the machine-readable activity signal than the second candidate heart rate, and the first candidate heart rate is output.

The technique described above allows the wearable heart rate monitoring device to independently assess the accuracy of the first candidate heart rate, and helps alleviate problems caused by improper motion correction. For example, it allows the wearable heart rate monitoring device to improve the accuracy of the estimated heart rate, in the case where a wearer's rate of motion or its harmonics closely matches the wearer's heart rate. Further, by adjusting the size of the search range depending on the wearer's rate and type of motion, the wearable heart rate monitoring device will be less likely to falsely measure a heart rate which is inconsistent with the wearer's activity (e.g., very high heart rate while walking), as can happen in low SNR scenarios.

Figure 6:
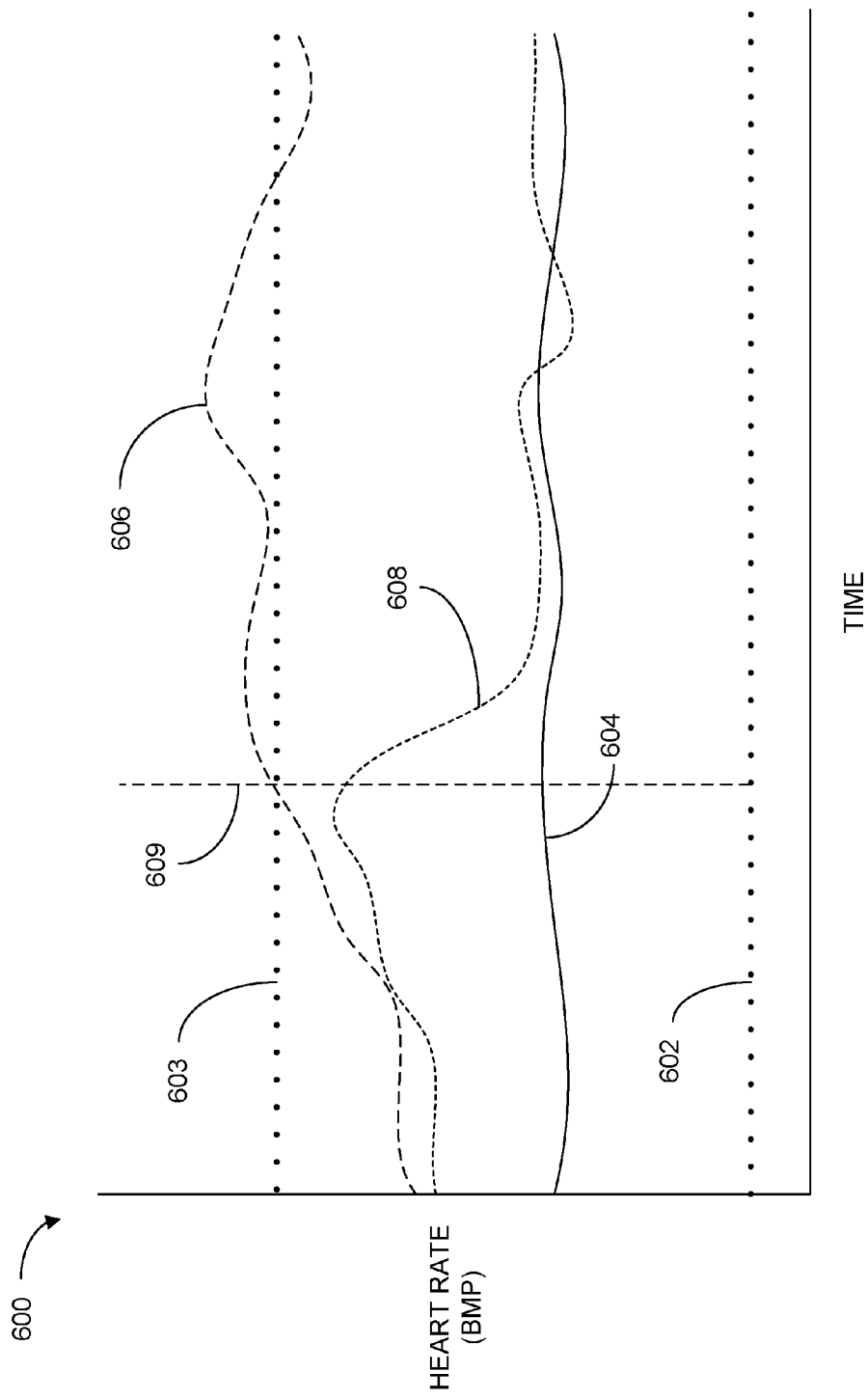
FIG. 6 shows a graph of a wearer's measured walking heart rate before and after correction.

FIG. 5 shows a graph 500 of a running heart rate of a wearer of a wearable heart rate monitoring device. Graph 500 includes frequency search window lower bound 502 and frequency search window upper bound 503. As described above, the range of the frequency search window may differ depending on the wearer's rate and type of motion. For example, lower bound 502 may be equal to the wearer's footfall frequency multiplied by a constant, and upper bound 503 may be equal to 200 bpm. Graph 500 further shows plot 504, indicating the wearer's actual heart rate over time, plot 506, indicating the estimated first candidate heart rate over time, and plot 508, indicating the estimated second candidate heart rate over time Prior to time indicator 509, plot 506 is consistently closer to plot 504 than plot 508. During this time, the wearable heart rate monitoring device may determine that the first candidate heart rate is more consistent with the machine-readable wearer activity signal than the second candidate heart rate, and output the first candidate heart rate. However, at time indicator 509, plot 506 suddenly diverges from plot 504. This may occur when, for example, the wearer's actual heart rate approaches the wearer's motion frequency, causing the actual heart rate to be filtered from the machine-readable heart rate signal during motion correction. Given that the first candidate heart rate drops below the lower bound 502 of the search window, the wearable heart rate monitoring device may determine the second candidate heart rate to be more consistent with the machine-readable wearer activity signal than the first candidate heart rate during the time interval between time indicators 509 and 510, and output the second candidate heart rate. A wearer of a heart rate monitoring device may be given more accurate heart rate estimates when the heart rate monitoring device selectively outputs either the first candidate or second candidate heart rate depending on which candidate heart rate is more consistent with the machine-readable activity signal at a given moment in time FIG. 6 shows a graph 600 of a walking heart rate of a wearer of a wearable heart rate monitoring device. Graph 600 includes a frequency search window, including a lower bound 602 and an upper bound 603. As described above, the range of the search window may differ depending on the wearer's rate and type of motion. For example, lower bound 602 may be equal to the wearer's footfall frequency, and upper bound 604 may be equal to twice the footfall frequency. Graph 600 further shows plot 604, indicating the wearer's actual heart rate over time, plot 606, indicating the estimated first candidate heart rate over time, and plot 608, indicating the estimated second candidate heart rate. As shown in graph 600, before time indicator 609, both the first and second candidate heart rates are initially somewhat higher than the wearer's actual heart rate, potentially because of signal noise that occurs at a frequency that falls within the frequency search window. At this time, with both candidate heart rates within the range of the search window, the wearable heart rate monitoring device may be configured to automatically output whichever candidate heart rate is determined to be more consistent with the machine-readable wearer activity signal based on one or more secondary considerations. As one example, the wearable heart rate monitoring device may automatically output the second candidate heart rate, given that the wearer is walking and the second candidate heart rate is lower than the first candidate heart rate.

After time indicator 609, plot 606 rises above upper bound 603. Accordingly, the wearable heart rate monitoring device may automatically identify a new highest occurrence frequency in the frequency search window, and select it as a new second candidate heart rate. Given that the first candidate heart rate is outside the range of the search window, the wearable heart rate monitoring device may determine the first candidate heart rate to be less consistent with the machine-readable activity signal than the newly identified second candidate heart rate. As shown, plot 608 closely tracks plot 604 after time indicator 609, indicating that the newly identified highest occurrence frequency may correspond to the actual heart rate. This further demonstrates that independently assessing the accuracy of the first candidate heart rate via the second estimation approach can improve heart rate estimation accuracy.

Figure 7:
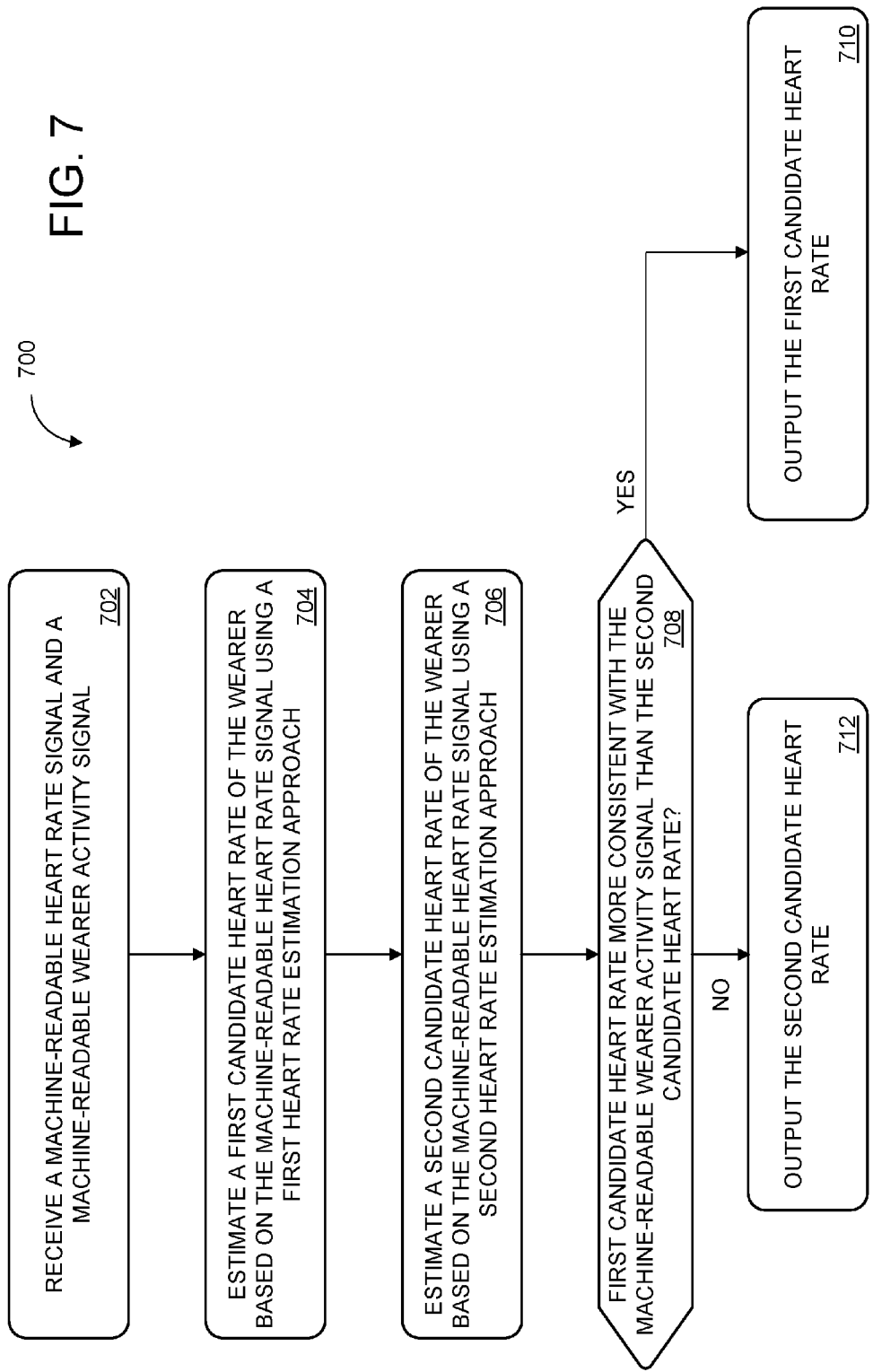
FIG. 7 shows an example method for estimating wearer heart rate.

FIG. 7 illustrates an example method 700 for monitoring a heart rate of a wearer of a wearable heart rate monitoring device. At 702, method 700 includes receiving a machine-readable heart rate signal and a machine-readable wearer activity signal. The machine-readable wearer activity signal may describe one or more aspects of a current activity of a wearer of the computing device. For example, it may indicate a machine-readable motion signal, it may indicate a type of activity currently being performed by the wearer, it may indicate a motion frequency of the wearer, and the motion frequency may indicate a footfall frequency of the wearer.

At 704, method 700 includes estimating a first candidate heart rate of the wearer based on the machine-readable heart rate signal using a first heart rate estimation approach. The first heart rate estimation approach may include generating a motion-corrected heart rate signal by filtering the wearer motion frequency from the machine-readable heart rate signal, and estimating the first candidate heart rate by evaluating an average length of time between crossings of a zero-axis by the motion-corrected heart rate signal.

At 706, method 700 includes estimating a second candidate heart rate of the wearer based on the machine-readable heart rate signal using a second heart rate estimation approach. As described above, the second heart rate estimation approach may include identifying a highest occurrence frequency within a frequency search window of the machine-readable heart rate signal for each of a plurality of time intervals, a range of the frequency search window varying according to the type of activity currently being performed by the wearer, and based on determining that a majority of the identified highest occurrence frequencies fall within a similarity threshold, selecting an average highest occurrence frequency as the second candidate heart rate.

At 708, method 700 includes determining whether the first candidate heart rate is more consistent with the machine-readable wearer activity signal than the second candidate heart rate. If yes, then method 700 proceeds to step 710, which includes outputting the first candidate heart rate. If no, then it is determined that the second candidate heart rate is more consistent with the machine-readable activity signal than the first candidate heart rate, and method 700 proceeds to step 712, which includes outputting the second candidate heart rate.

In some embodiments, the methods and processes described herein may be tied to a sensory-and-logic system of one or more machines. Such methods and processes may be implemented as a computer-application program or service, an application-programming interface (API), a library, firmware, and/or other computer-program product. FIGS. 1A and 1B show one, non-limiting example of a sensory-and-logic system to enact the methods and processes described herein. However, these methods and process may also be enacted on sensory-and-logic systems of other configurations and form factors, as shown schematically in FIG. 8.

Figure 8:
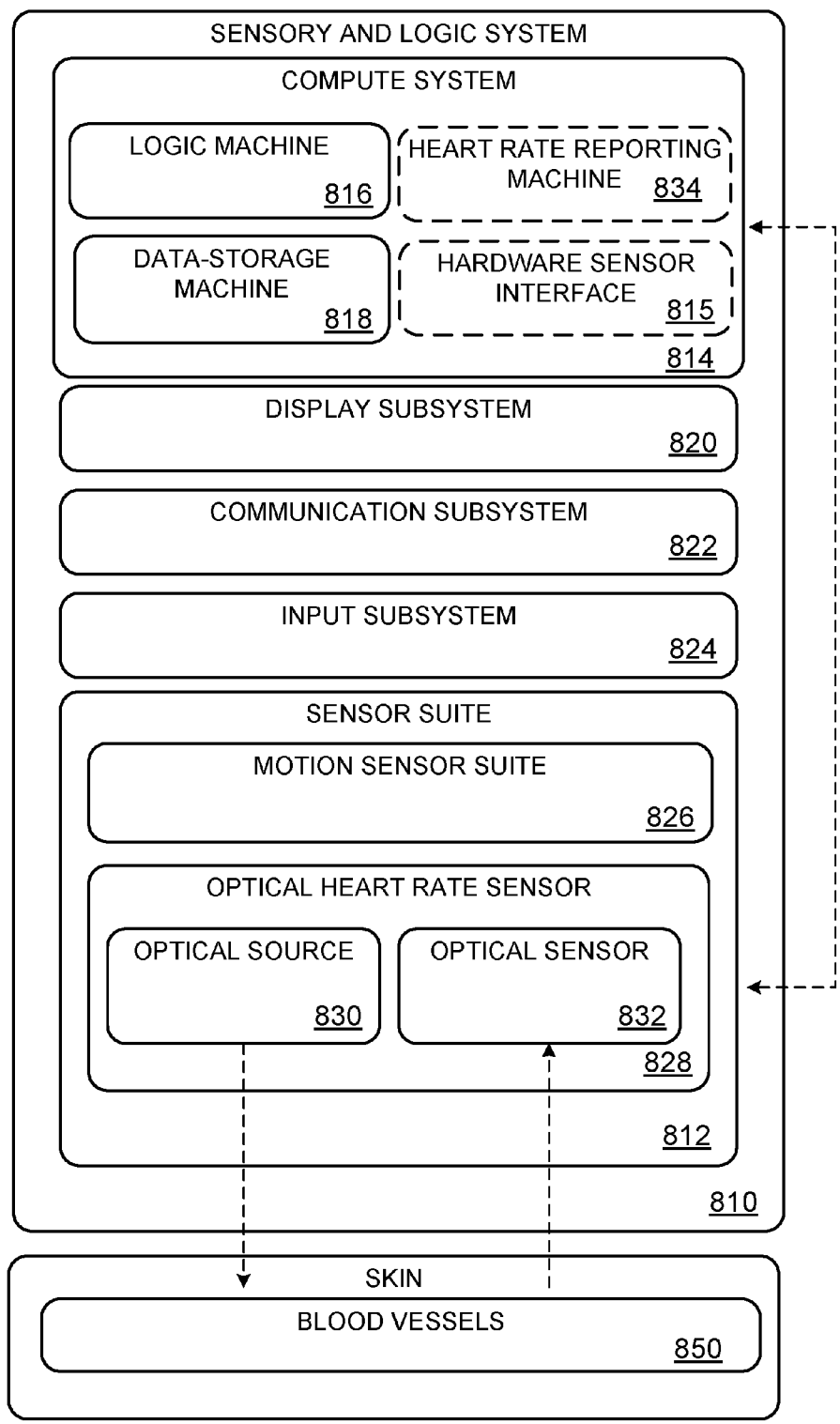
FIG. 8 schematically shows an example computing system.

FIG. 8 schematically shows a form-agnostic sensory-and-logic system 810 that includes a sensor suite 812 operatively coupled to a compute system 814. The compute system may include a hardware sensor interface 815 configured to receive inputs from sensors included in sensor suite 812. The compute system includes a logic machine 816 and a data-storage machine 818. The compute system is operatively coupled to a display subsystem 820, a communication subsystem 822, an input subsystem 824, and/or other components not shown in FIG. 8.

Logic machine 816 includes one or more physical devices configured to execute instructions. The logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

Logic machine 816 may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of a logic machine optionally may be distributed among two or more separate devices, which may be remotely located and/or configured for coordinated processing. Aspects of a logic machine may be virtualized and executed by remotely accessible, networked computing devices in a cloud-computing configuration.

Data-storage machine 818 includes one or more physical devices configured to hold instructions executable by logic machine 816 to implement the methods and processes described herein. When such methods and processes are implemented, the state of the data-storage machine may be transformed e.g., to hold different data. The data-storage machine may include removable and/or built-in devices; it may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. The data-storage machine may include volatile, nonvolatile, dynamic, static, read/write, read-only, random-access, sequential-access, location-addressable, file-addressable, and/or content-addressable devices.

Data-storage machine 818 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 816 and data-storage machine 818 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

Display subsystem 820 may be used to present a visual representation of data held by data-storage machine 818. This visual representation may take the form of a graphical user interface (GUI). As the herein described methods and processes change the data held by the storage machine, and thus transform the state of the storage machine, the state of display subsystem 820 may likewise be transformed to visually represent changes in the underlying data. Display subsystem 820 may include one or more display subsystem devices utilizing virtually any type of technology. Such display subsystem devices may be combined with logic machine 816 and/or data-storage machine 818 in a shared enclosure, or such display subsystem devices may be peripheral display subsystem devices. Display 20 of FIGS. 1A and 1B is an example of display subsystem 820.

Communication subsystem 822 may be configured to communicatively couple compute system 814 to one or more other computing devices. The communication subsystem may include wired and/or wireless communication devices compatible with one or more different communication protocols. As non-limiting examples, the communication subsystem may be configured for communication via a wireless telephone network, a local- or wide-area network, and/or the Internet. Communication suite 24 of FIGS. 1A and 1B is an example of communication subsystem 822.

Input subsystem 824 may comprise or interface with one or more user-input devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity. Touch-screen sensor 32 and push buttons 34 of FIGS. 1A and 1B are examples of input subsystem 824.

Sensor suite 812 may include one or more different sensors—e.g., a touch-screen sensor, push-button sensor, microphone, visible-light sensor, ultraviolet sensor, ambient-temperature sensor, contact sensors, and/or GPS receiver—as described above with reference to FIGS. 1A and 1B. Sensor suite 812 may include motion sensor suite 826. Motion sensor suite 826 may include one or more of an accelerometer, gyroscope, magnetometer, or other suitable motion detectors. Sensor suite 812 may further include optical heart rate sensor 828. As described herein, optical heart rate sensor 828 may include optical source 830 and optical sensor 832. Optical source 830 may comprise one or more LED emitters, for example, while optical sensor 832 may comprise one or more photodiodes matched to detect light at frequencies that are based on the frequencies of light output by the optical source. Optical source 830 may be configured to illuminate one or more blood vessels 850 through the skin 852 of the wearer, and optical sensor 832 may be configured to measure illumination reflected from or transmitted through blood vessels 850.

Compute system 814 may include one or more hardware sensor interfaces 815, configured to receive and process inputs from one or more sensors of the sensor suite. Furthermore, compute system 814 may include heart rate reporting machine 834, which may be communicatively coupled to logic machine 816 and data-storage machine 818 and perform one or more of the heart rate estimation, evaluation, and output processes described above. Heart rate reporting machine 834 may receive raw signals from optical sensor 832 via one or more hardware sensor interfaces, and may further process the raw signals to determine heart rate, caloric expenditures, etc. Processed signals may be stored and output via heart rate reporting machine 834, and/or other components of compute system 814. Control signals sent to optical source 830 and optical sensor 832 may be based on signals received from optical sensor 832, signals derived from sensor suite 812, information stored in data-storage machine 818, input received from communication subsystem 822, input received from input subsystem 824, etc.

In an example, a computing device comprises: a hardware sensor interface configured to receive a machine-readable heart rate signal and a machine-readable wearer activity signal describing one or more aspects of a current activity of a wearer of the computing device; and a heart rate reporting machine configured to: estimate a first candidate heart rate of the wearer based on the machine-readable heart rate signal using a first heart rate estimation approach; estimate a second candidate heart rate of the wearer based on the machine-readable heart rate signal using a second heart rate estimation approach different than the first heart rate estimation approach; and based on determining that the first candidate heart rate is more consistent with the machine-readable wearer activity signal than the second candidate heart rate, output the first candidate heart rate; or based on determining that the second candidate heart rate is more consistent with the machine-readable wearer activity signal than the first candidate heart rate, output the second candidate heart rate. In this example or any other example, the machine-readable wearer activity signal is usable to determine a type of activity currently being performed by the wearer. In this example or any other example, the machine-readable wearer activity signal indicates a wearer motion frequency indicating a current rate of motion of the wearer. In this example or any other example, the wearer motion frequency indicates a footfall frequency of the wearer. In this example or any other example, the first heart rate estimation approach includes: generating a motion-corrected heart rate signal by filtering the wearer motion frequency from the machine-readable heart rate signal; and estimating the first candidate heart rate by evaluating an average length of time between crossings of a zero-axis by the motion-corrected heart rate signal. In this example or any other example, the second heart rate estimation approach includes: identifying a highest occurrence frequency within a frequency search window of the machine-readable heart rate signal for each of a plurality of time intervals, a range of the frequency search window varying according to the type of activity currently being performed by the wearer; and based on determining that a majority of the identified highest occurrence frequencies fall within a similarity threshold, selecting an average highest occurrence frequency as the second candidate heart rate. In this example or any other example, based on determining the type of activity to be walking, a lower bound of the frequency search window is set equal to a footfall frequency of the wearer, and an upper bound of the frequency search window is set equal to twice the footfall frequency of the wearer. In this example or any other example, based on determining the type of activity to be running, a lower bound of the frequency search window is set equal to a footfall frequency of the wearer multiplied by a constant, and an upper bound of the frequency search window is set equal to 200 bpm. In this example or any other example, the second candidate heart rate is determined to be more consistent with the machine-readable wearer activity signal than the first candidate heart rate when the type of activity is determined to be walking and the second candidate heart rate is lower than the first candidate heart rate. In this example or any other example, the second candidate heart rate is determined to be more consistent with the machine-readable wearer activity signal than the first candidate heart rate when the type of activity is determined to be running and a difference between the second candidate heart rate and twice the motion frequency is greater than a running disparity threshold. In this example or any other example, the running disparity threshold is equal to 10 beats per minute.

In an example, a wearable heart rate monitoring device comprises: an optical sensor configured to translate test light reflected from a wearer of the wearable heart rate monitoring device into a machine-readable heart rate signal; a motion sensor configured to translate motion of the wearable heart rate monitoring device into a machine-readable motion signal; and a heart rate reporting machine configured to: motion-correct the machine-readable heart rate signal to a motion-corrected heart rate signal based on the machine-readable motion signal; estimate a first candidate heart rate of the wearer from a time domain representation of the motion-corrected heart rate signal using a first heart rate estimation approach; estimate a second candidate heart rate of the wearer from a frequency domain representation of the motion-corrected heart rate signal using a second heart rate estimation approach different from the first heart rate estimation approach; based on the machine-readable motion signal, determine a type of activity of the wearer of the wearable heart rate monitoring device; and based on determining that the first candidate heart rate is more consistent with the type of activity than the second candidate heart rate, output the first candidate heart rate; or based on determining that the second candidate heart rate is more consistent with the type of activity than the first candidate heart rate, output the second candidate heart rate. In this example or any other example, the machine-readable motion signal indicates a footfall frequency of the wearer. In this example or any other example, the first heart rate estimation approach includes estimating the first candidate heart rate by evaluating an average length of time between crossings of a zero-axis by the time domain representation of the motion-corrected heart rate signal. In this example or any other example, the second heart rate estimation approach includes: identifying a highest occurrence frequency within a frequency search window of the frequency domain representation of the motion-corrected heart rate signal for each of a plurality of time intervals, a range of the frequency search window varying according to the type of activity currently being performed by the wearer; and based on determining that a majority of the identified highest occurrence frequencies fall within a similarity threshold, selecting an average highest occurrence frequency as the second candidate heart rate. In this example or any other example, the second candidate heart rate is determined to be more consistent with the machine-readable motion signal than the first candidate heart rate when the type of activity is determined to be walking and the second candidate heart rate is lower than the first candidate heart rate. In this example or any other example, the second candidate heart rate is determined to be more consistent with the machine-readable motion signal than the first candidate heart rate when the type of activity is determined to be running and a difference between the second candidate heart rate and twice a motion frequency of the wearer is greater than a running disparity threshold of 10 beats per minute.

In an example, a wearable heart rate monitoring device comprises: an optical sensor configured to translate test light reflected from a wearer of the wearable heart rate monitoring device into a machine-readable heart rate signal; a motion sensor configured to translate motion of the wearable heart rate monitoring device into a machine-readable motion signal; and a heart rate reporting machine configured to: determine a type of activity currently being performed by the wearer of the wearable heart rate monitoring device based at least in part on the machine-readable motion signal; and output an estimated heart rate based on at least the machine-readable heart rate signal and the type of activity. In this example or any other example, the machine-readable motion signal indicates a footfall frequency of the wearer. In this example or any other example, the type of activity is either walking or running It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A computing device, comprising:
   a hardware sensor interface configured to receive a machine-readable heart rate signal and a machine-readable wearer activity signal describing one or more aspects of a current activity of a wearer of the computing device; and
   a heart rate reporting machine configured to:
      estimate a first candidate heart rate of the wearer based on the machine-readable heart rate signal using a first heart rate estimation approach;
      estimate a second candidate heart rate of the wearer based on a frequency domain transformation of the machine-readable heart rate signal using a second heart rate estimation approach different than the first heart rate estimation approach; and
      output the first candidate heart rate when the first candidate heart rate is more consistent with the machine-readable wearer activity signal than the second candidate heart rate; or
      output the second candidate heart rate when the second candidate heart rate is more consistent with the wearer activity signal than the first candidate heart rate.

2. The computing device of claim 1, where the machine-readable wearer activity signal is usable to determine a type of activity currently being performed by the wearer.

3. The computing device of claim 2, where the machine-readable wearer activity signal indicates a wearer motion frequency indicating a current rate of motion of the wearer.

4. The computing device of claim 3, where the wearer motion frequency indicates a footfall frequency of the wearer.

5. The computing device of claim 3, where the first heart rate estimation approach includes:
   generating a motion-corrected heart rate signal by filtering the wearer motion frequency from the machine-readable heart rate signal; and
   estimating the first candidate heart rate by evaluating an average length of time between crossings of a zero-axis by the motion-corrected heart rate signal.

6. The computing device of claim 2, where the second heart rate estimation approach includes:
   identifying a highest occurrence frequency within a frequency search window of the machine-readable heart rate signal for each of a plurality of time intervals, a range of the frequency search window varying according to the type of activity currently being performed by the wearer; and
   based on determining that a majority of the identified highest occurrence frequencies fall within a similarity threshold, selecting an average highest occurrence frequency as the second candidate heart rate.

7. The computing device of claim 6, where based on determining the type of activity to be walking, a lower bound of the frequency search window is set equal to a footfall frequency of the wearer, and an upper bound of the frequency search window is set equal to twice the footfall frequency of the wearer.

8. The computing device of claim 6, where based on determining the type of activity to be running, a lower bound of the frequency search window is set equal to a footfall frequency of the wearer multiplied by a constant, and an upper bound of the frequency search window is set equal to 200 bpm.

9. The computing device of claim 2, where the second candidate heart rate is determined to be more consistent with the machine-readable wearer activity signal than the first candidate heart rate when the type of activity is determined to be walking and the second candidate heart rate is lower than the first candidate heart rate.

10. The computing device of claim 3, where the second candidate heart rate is determined to be more consistent with the machine-readable wearer activity signal than the first candidate heart rate when the type of activity is determined to be running and a difference between the second candidate heart rate and twice the motion frequency is greater than a running disparity threshold.

11. The computing device of claim 10, where the running disparity threshold is equal to 10 beats per minute.

12. A wearable heart rate monitoring device, comprising:
   an optical sensor configured to translate test light reflected from a wearer of the wearable heart rate monitoring device into a machine-readable heart rate signal;
   a motion sensor configured to translate motion of the wearable heart rate monitoring device into a machine-readable motion signal; and
   a heart rate reporting machine configured to:
      motion-correct the machine-readable heart rate signal to a motion-corrected heart rate signal based on the machine-readable motion signal;
      estimate a first candidate heart rate of the wearer from a time domain representation of the motion-corrected heart rate signal using a first heart rate estimation approach;
      estimate a second candidate heart rate of the wearer from a frequency domain representation of the motion-corrected heart rate signal using a second heart rate estimation approach different from the first heart rate estimation approach;
      determine a type of activity of the wearer of the wearable heart rate monitoring device from the machine-readable motion signal; and
      output the first candidate heart rate when the first candidate heart rate is more consistent with the machine-readable motion signal than the second candidate heart rate; or
      output the second candidate heart rate when the second candidate heart rate is more consistent with the machine-readable motion signal than the first candidate heart rate.

13. The wearable heart rate monitoring device of claim 12, where the machine-readable motion signal indicates a footfall frequency of the wearer.

14. The wearable heart rate monitoring device of claim 12, where the first heart rate estimation approach includes estimating the first candidate heart rate by evaluating an average length of time between crossings of a zero-axis by the time domain representation of the motion-corrected heart rate signal.

15. The wearable heart rate monitoring device of claim 12, where the second heart rate estimation approach includes:
   identifying a highest occurrence frequency within a frequency search window of the frequency domain representation of the motion-corrected heart rate signal for each of a plurality of time intervals, a range of the frequency search window varying according to the type of activity currently being performed by the wearer; and based on determining that a majority of the identified highest occurrence frequencies fall within a similarity threshold, selecting an average highest occurrence frequency as the second candidate heart rate.

16. The wearable heart rate monitoring device of claim 12, where the second candidate heart rate is determined to be more consistent with the machine-readable motion signal than the first candidate heart rate when the type of activity is determined to be walking and the second candidate heart rate is lower than the first candidate heart rate.

17. The wearable heart rate monitoring device of claim 12, where the second candidate heart rate is determined to be more consistent with the machine-readable motion signal than the first candidate heart rate when the type of activity is determined to be running and a difference between the second candidate heart rate and twice a motion frequency of the wearer is greater than a running disparity threshold of 10 beats per minute.

18. A wearable heart rate monitoring device, comprising:
an optical sensor configured to translate test light reflected from a wearer of the wearable heart rate monitoring device into a machine-readable heart rate signal;
a motion sensor configured to translate motion of the wearable heart rate monitoring device into a machine-readable motion signal; and
a heart rate reporting machine configured to:
determine a type of activity currently being performed by the wearer of the wearable heart rate monitoring device from the machine-readable motion signal; and
output an estimated heart rate from a frequency domain transformation of the machine-readable heart rate signal and the type of activity.

19. The wearable heart rate monitoring device of claim 18, where the machine-readable motion signal indicates a footfall frequency of the wearer.

20. The wearable heart rate monitoring device of claim 18, where the type of activity is either walking or running.

* * * * *